Feb. 1, 1938. L. BURBANK Plant Pat. 269
ROSE
Filed May 8, 1937
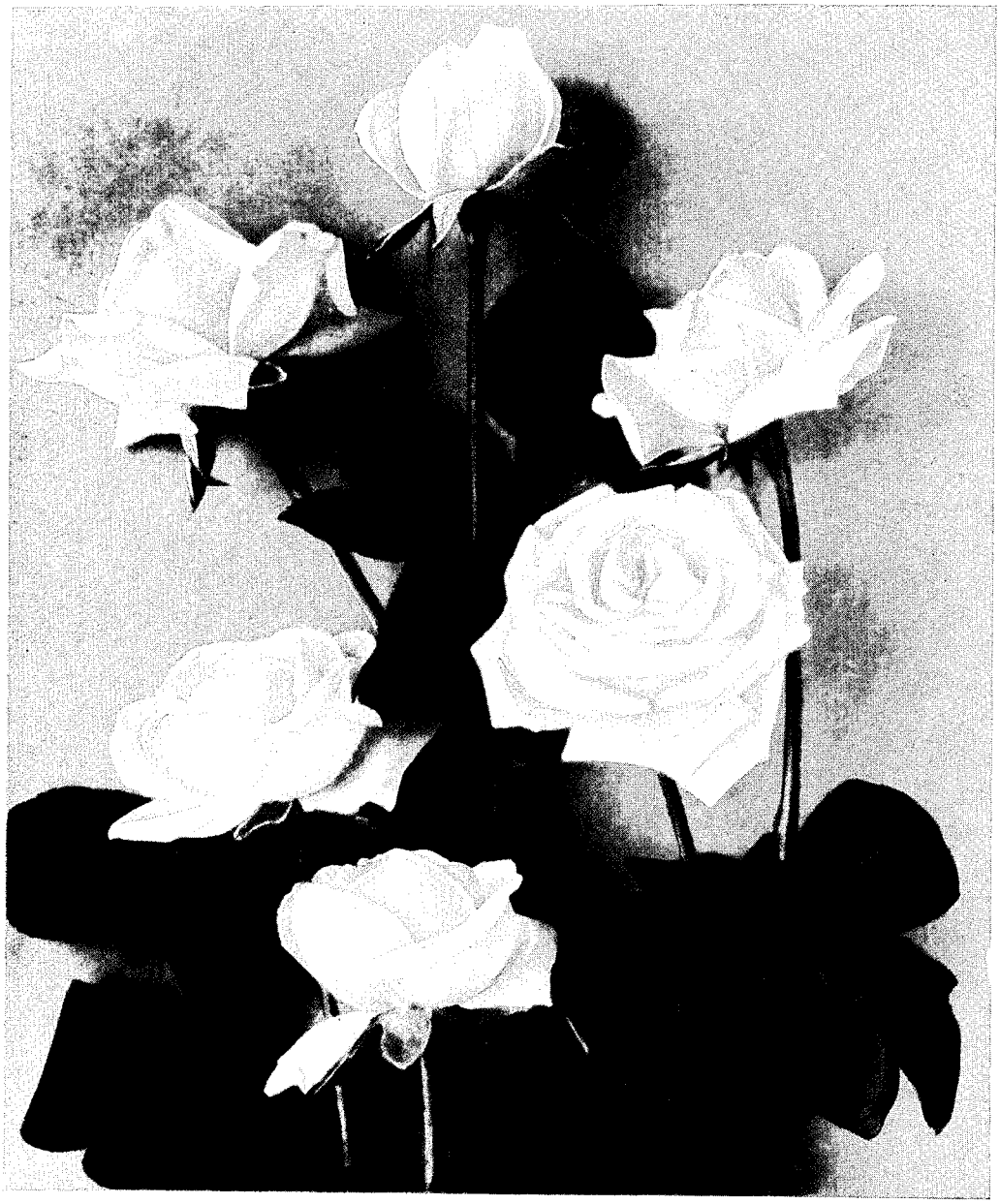
Inventor
Luther Burbank
By Elizabeth Waters Burbank
Executrix of the estate of Luther Burbank
(deceased)
By Robbs & Robbs
Attorneys Patented Feb. 1, 1938

Plant Pat. 269

UNITED STATES PATENT OFFICE

269

ROSE

Luther Burbank, deceased, late of Santa Rosa, Calif., by Elizabeth Waters Burbank, executrix, Santa Rosa, Calif., assignor to Stark Bro's Nurseries & Orchards Company, Louisiana, Mo.

Application May 8, 1937, Serial No. 141,545

1 Claim. (Cl. 47—61)

This invention relates to a new and distinct variety of rose plant, resulting from a definite effort to improve existing garden roses.

The variety represents a new type of everblooming garden rose and may be considered for general purposes, according to the terminology of the American Rose Society, as a hybrid tea, originating as a self-seedling of the well known climbing rose "Dr. W. Van Fleet". It is well known that there has long been a desire for a rose of a similar character, but of bush form, and this new variety fulfills this desideratum.

In general, it may be noted that the present variety is similar to the Dr. W. Van Fleet in color values and appearance of its bloom, but is distinguished from said known variety in its bush instead of climbing form; in its everblooming habit, being a constant recurrent bloomer producing flowers throughout the season, profusely as usual during the early months, but constantly during the long season, where Dr. W. Van Fleet under comparable conditions blooms only during the spring months.

Aside from this comparison, the new variety is characterized particularly by the stronger, hardier, healthier, attractive plant which furnishes a greater quantity of flowers than any other dwarf hybrid tea of similar color.

A further important characteristic is its great resistance to heat and drouth, as indicated by its continuing to bloom profusely through the hottest summer on record in the test gardens and during the accompanying very severe drouth and hot withering winds.

Asexual reproduction of the variety shows the characteristics referred to in the foregoing are fixed.

The following is a detail description of the new variety, color designations being in accord with Ridgway's Color Standard except where obviously the ordinary dictionary definition is meant:—

Observations were made in test gardens at Louisiana, Missouri, during the longest, hottest summer on record (1936) and most severe and prolonged drouth with only 1½" of rain from May until September.

Classification:

Hybrid tea.

Parentage:

Seedling of Dr. W. Van Fleet.

*Flower*

Blooming habit:

Blooms profusely from early spring until frost.

*Recurrent.*—Continuous.

Bud:

*Size.*—Medium; 1¼ inches (blooms larger in normal years).

*Form.*—Ovoid.

*Color.*—General tonality—flesh pink, shaded from inside out. When sepals first divide—lighter than Venetian pink.

When sepals unfurl:

Outer petals—lighter than Venetian pink.

Inner petals—Venetian pink.

When half bloom:

Inside of petals—lighter than Venetian pink to white.

Reverse of petals—lighter than Venetian pink.

*Sepals.*—Smooth, curl back as flower opens.

*Calyx.*—Shape—funnel. Size—¾ inch long, Aspect—smooth.

*Pedicel.*—Length—3¼ inches, Calyx to first leaf—3 to 3¼ inches. Aspect—rough. Color—light green, bronzy. Strength—erect.

*Opening.*—Opens well, unaffected by conditions.

Bloom:

*Size.*—Medium; full expanded average 3½ inches.

*Borne.*—Singly.

*Form.*—When first open, high centered. Permanence—curls outwardly. Sides, outer at angles. Tops notched.

*Stems.*—Strong. Length—10 to 12 inches.

*Petalage.*—Very double (many petals and stamens hidden).

*Color.*—Blending from deeper than Venetian pink inside to much lighter than Venetian pink on outer unfurled petals. Tonality from distance—blending of flesh pink. Center—deeper than Venetian pink. Outer—lighter than Venetian pink.

*Variegations.*—None.

*Discoloration.*—Proper tonality of base—light shade of pink to creamy white. End of first and second days—no discoloration. Thereafter—slightly lighter pink.

Petals:

*Texture.*—Thick.

*Appearance.*—Satiny.

*Form.*—Round, notched, curved outwardly. Tips—outcurved.

*Arrangement.*—Irregular. Petaloids—few.

*Persistence.*—Hang on.

*Fragrance.*—Moderate. Nature—"Old Rose" perfume (Centifolia).

*Lasting quality.*—On plant—long; average 7 days in October. As cut flower—long; average 3 days in October.

Sexual organs:

*Stamens, anthers.*—Medium size. Color—yellow. Arrangement—regular around styles.

*Filaments (threads).*—Short. Color—yellow.

*Pollen.*—Gold.

*Styles.*—Bunched, medium length.

*Stigmas.*—Yellow

*Ovaries.*—All inside.

*Plant*

Form:

Bush.

Growth:

Upright, shapely.

Average growth year 18 to 20 inches from spring to fall.

Continuous.

*Appearance.*—General appearance of a Bush Van Fleet.

*Hardiness.*—No injury at temperature 18 degrees below zero.

Foliage:

*Number of leaflets.*—5 to 7.

*Size.*—Medium, 3½ inches. End leaflet 1¾ inches to 1⅜ inches.

*Quantity.*—Normal.

*Color.*—New foliage—bronzy. Old foliage—medium green.

*Shape.*—Oval.

*Texture.*—Upper side—glossy. Under side—smooth. Ribs and veins—medium.

*Edges.*—Serrated. Serration—single, medium, sharp.

*Rachis.*—Color—reddish. Under side—prickles.

*Stipules.*—Short.

*Disease resistance.*—Slightly susceptible to black spot and aphis. Not especially susceptible to any diseases.

Wood:

*New wood.*—*Color*—light green.

Thorns:

*Quantity on main base stalks.*—Few.

*Form.*—Base is oval.

*Color.*—Red.

*Position.*—Irregular.

What is claimed is:

A new and distinct variety of hybrid tea rose plant characterized as to novelty by the bush or dwarf form, its strength, hardiness and resistance to heat and drouth, its everblooming habit and the profuseness of flowers compared with hybrids of similar color, substantially as shown and described.

ELIZABETH WATERS BURBANK,

*Executrix of the Estate of Luther Burbank, Deceased.*